United States Patent
(12)
June (10) Patent No.: US 6,320,073 B1
(45) Date of Patent: Nov. 20, 2001

(54) PROCESS FOR SEPARATION OF THE DIPOTASSIUM SALT OF NAPHTHALENE DICARBOXYLIC ACID USING ACTIVATED CARBON BEDS

(75) Inventor: Raymond Lawrence June, Singapore (SG)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/643,477

(22) Filed: Aug. 22, 2000

Related U.S. Application Data (60) Provisional application No. 60/151,589, filed on Aug. 30, 1999, provisional application No. 60/151,577, filed on Aug. 30, 1999, provisional application No. 60/151,607, filed on Aug. 30, 1999, provisional application No. 60/151,498, filed on Aug. 30, 1999, provisional application No. 60/151,602, filed on Aug. 30, 1999, provisional application No. 60/151,603, filed on Aug. 30, 1999, provisional application No. 60/151,529, filed on Aug. 30, 1999, provisional application No. 60/151,489, filed on Aug. 30, 1999, provisional application No. 60/151,604, filed on Aug. 30, 1999, provisional application No. 60/151,606, filed on Aug. 30, 1999, provisional application No. 60/151,497, filed on Aug. 30, 1999, provisional application No. 60/151,590, filed on Aug. 30, 1999, and provisional application No. 60/151,578, filed on Aug. 30, 1999.

(51) Int. Cl.$^7$ .................................................. C07C 51/42
(52) U.S. Cl. ............................................................ 562/485
(58) Field of Search .................................... 562/481, 485, 562/486

(56) References Cited

U.S. PATENT DOCUMENTS

| | | | |
|---|---|---|---|
| 2,823,231 | 2/1958 | Raecke et al. ........................ 260/515 |
| 3,069,470 | 12/1962 | Fieck et al. ........................... 260/582 |
| 3,671,578 | 6/1972 | Ogata et al. ....................... 260/515 P |
| 3,766,258 | 10/1973 | Engelbrecht et al. ............ 260/515 P |
| 3,954,840 | * 5/1976 | Yamashita et al. . |
| 4,480,129 | 10/1984 | Priegnitz et al. ..................... 564/424 |
| 4,642,397 | 2/1987 | Zinnen et al. ....................... 568/934 |
| 5,622,682 | 4/1997 | Tom ..................................... 423/230 |
| 5,728,870 | * 3/1998 | Holzhauer et al. . |
| 5,770,764 | 6/1998 | Zeitlin et al. ........................ 562/412 |
| 5,779,998 | 7/1998 | Tom ..................................... 423/210 |
| 5,859,294 | * 1/1999 | Hashimoto . |
| 6,214,241 | * 4/2001 | Miura . |

FOREIGN PATENT DOCUMENTS 864587 9/1998 (CA) .

* cited by examiner

Primary Examiner—Paul J. Killos
Assistant Examiner—John N. Calve
(74) Attorney, Agent, or Firm—Kim Muller (57) ABSTRACT

In a process for producing aromatic dicarboxylic acids which incorporates the disproportionation of a salt of an aromatic mono- or dicarboxylic acid to produce the unreacted salt of an aromatic mono- or dicarboxylic acid and the salt of the desired aromatic dicarboxylic acid, a method is disclosed for separating the salt of the desired product from the unreacted salt which comprises passing both said unreacted salt and said salt of the desired product in an aqueous solution over an adsorbent comprising an activated carbon. The process is particularly suitable for separating potassium naphthoate from 2,6-K2NDA after potassium naphthoate is disproportionated to produce 2,6-K2NDA and 1- or 2-potassium naphthoate. The adsorbent can be regenerated by the use of a displacing agent and reused without off site regeneration.

20 Claims, 5 Drawing Sheets

Fig. 5

PROCESS FOR SEPARATION OF THE DIPOTASSIUM SALT OF NAPHTHALENE DICARBOXYLIC ACID USING ACTIVATED CARBON BEDS

CROSS REFERENCE

This application claims the benefit of U.S. Provisional Application No. 60/151,589, filed Aug. 30, 1999, the entire disclosure of which is hereby incorporated by reference.

This application is related to U.S. application Ser. Nos. 60/151,577, 60/151,607, 60/151,498, 60/151,602, 60/151,603, 60/151,529, 60/151,489, 60/151,604, 60/151,606, 60/151,497, 60/151,590, and 60/151,578, filed of even date.

FIELD OF THE INVENTION

This invention relates to the purification of 2,6-napthalene dicarboxylic acid. More particularly, this invention relates to a method for separating and recycling unreacted feed from desired product in a process for preparing aromatic dicarboxylic acids of the type which incorporates a disproportionation or rearrangement reaction. In the preferred embodiment, this invention relates to the separation of a salt of naphthoic acid from an aqueous solution containing the disproportionation reaction product comprising the dipotassium salt of 2,6 naphthalene dicarboxylic acid, 2,6 K2NDA, by passing said aqueous solution over activated carbon. It also relates to a method of regenerating the activated carbon beds in place.

BACKGROUND OF THE INVENTION

Aromatic carboxylic acids are highly useful organic compounds. They are useful as intermediates for the preparation of other organic compounds, and as monomers for the preparation of polymeric materials. In particular, the naphthalene dicarboxylic acids are used for preparing photographic chemicals and dyestuffs. Naphthalene dicarboxylic acids can be also be used to prepare a variety of polyester and polyamide compositions. 2,6-naphthalene dicarboxylic acid (hereafter referred to as 2,6-NDA) is a particularly useful aromatic carboxylic acid which can be reacted with ethylene glycol to prepare poly(ethylene-2,6-naphthalate). Polyesters prepared from 2,6-NDA have excellent heat resistance, gas barrier, and mechanical properties. Therefore, much research in the art has focused on methods of preparing 2,6-NDA. Most of the methods for making 2,6-NDA involve numerous steps, many of which address purification of the product.

It is known in the art to produce the crude dialkali salt of naphthalene-2,6-dicarboxylic acid by heating alkali naphthalene-α-monocarboxylate(alkali 1-naphthoate), alkali naphthalene-β-monocarboxylate(alkali 2-naphthoate), or mixtures thereof at high temperatures in carbon dioxide or other gaseous atmosphere, (German Pat. No. 953,072) or by similarly heating dialkali naphthalene 1,8 dicarboxylate (German Pat. Nos. 932,125 and 1,002,316). This reaction is usually referred to as a Henkel disproportionation reaction and produces a product consisting mainly of a single thermodynamically favored disalt product. It is known in the art to prepare the alkali salts used in this reaction by heating naphthalene α-monocarboxylic acid, naphthalene β-monocarboxylic acid, or naphthalene 1,8-dicarboxylic acid, with hydroxides, carbonates, bicarbonates, etc. of alkali metals in an aqueous medium under heating. When potassium naphthoate is the feed in a Henkel disproportionation reaction, the product is the salt of the desired 2,6-NDA, 2,6-K2NDA. In addition to the desired product, this reaction also typically produces unreacted potassium naphthoate and 2,3 K2NDA. (In describing the invention certain abbreviations will be used which have the following meanings: KNA=potassium naphthoate; 2,6-K2NDA=dipotassium salt of 2,6-naphthalene dicarboxylic acid; and 2,6-NDA=2,6-naphthalene dicarboxylic acid.)

Methods of separating the desired disalts of 2,6-naphthalene dicarboxylic acid are known. After the Henkel disproportionation reaction, the total reactor effluent is generally dissolved in water to separate out the aromatic core molecule produced by the Henkel disproportionation and the catalyst as separate phases with the unconverted feed and the desired reaction product dissolved in the aqueous phase. In one method known in the art, the disproportionation reaction product, containing the dialkali salt of NDA and the salt of naphthalene mono- or di-carboxylic acid, is dissolved in water, and the water insoluble matters are filtered off. Then a mineral acid is added to the system to release naphthalene carboxylic acids. The free acids are recovered from the system by filtration and are further boiled with an organic solvent such as a lower aliphatic carboxylic acid to separate 2,6-NDA which is insoluble in the organic solvent, from the free dicarboxylic acids which have been separated from the aforementioned unreacted products and side products upon addition of a mineral acid, and are soluble in organic solvent. A disadvantage of this method is that the side product alkali salt of a mineral acid cannot be directly re-used in the preparation of starting material for the disproportionation reaction. (See U.S. Pat. Nos. 2,823,231 and 3,671,578.)

CA 864587 discloses a method for separating 2,6-NDA by disproportionating the alkali salt of 2,6-NDA by heating it in water or water-containing organic solvent to form free 2,6-NDA and by-product dialkali salt, where the former is precipitated.

One method of purifying 2,6-K2NDA to acceptable levels of potassium naphthoate is by performing two successive crystallizations on the crude 2,6-K2NDA from the disproportionation reaction. This process is energy intensive because the water solubility of 2,6-K2NDA varies only weakly with temperature and the product must be recovered by an evaporative crystallization step which involves evaporating about half of the water charged to the crystallizer. Furthermore, laboratory experiments have shown that the crystallization process cannot recover 2,6-K2NDA in high yield from the crystallization when larger than normal levels of impurities are present in the crystallization feed due to co-precipitation of the impurities with the product 2,6-K2NDA.

None of the references in the art pertaining to production and purification of 2,6-NDA teach the use of activated carbon for separating unreacted feed from product aromatic dicarboxylic acids. U.S. Pat. No. 5,770,764 does disclose the use of carbon beds to remove impurities. In '764 the 2,6-NDA is made by direct oxidation and the carbon bed is used to remove impurities such as trimellitic acid, bromo-2,6-NDA, 2-formyl-6-naphthoic acid, 2 naphthoic acid, other impurities and cobalt and manganese catalyst components.

It is known in the art to use cyclic adsorption to purify petrochemical products. For example, U.S. Pat. No. 3,069,470 discloses the use of type X zeolites for the separation of the meta isomer from other isomers of toluidine.

From U.S. Pat. No. 4,480,129 it is known that X and Y type zeolites, exchanged with transition metals, are paraselective in a mixture of isomers of toluidine.

U.S. Pat. No. 4,642,397 discloses that an adsorbent comprising an X or Y type zeolite cation exchanged with a cation selected from the group K, Na, Ca, Ba, Li, or Mg can be employed to selectively separate 2,4-dinitrotoluene from a feed mixture comprising 2,4-dinitrotoluene and at least one other isomer.

In U.S. Pat. Nos. 5,622,682 and 5,779,998 adsorbents are employed to recover halocarbons from a gas mixture.

Where activated carbon has been used in the art, it is typically used to adsorb trace levels of materials from a solution, rather than percent level impurities in the presence of in the range of ten times excess of a very similar molecule.

Known methods of separating unreacted feed components from 2,6-K2NDA require a number of steps. The prior art for 2,6-NDA purification made by a disproportionation reaction is crystallization or precipitation with carbon dioxide and often the potassium naphthoate is separated in a form which is not recyclable. Therefore, there is a need in the art for a simpler process for separating unreacted feed such as potassium naphthoate from 2,6-K2NDA. This would be a distinct advance in the art relating to purification of 2,6-NDA.

The present invention provides such a process. Other objects and advantages of the invention will be apparent to those skilled in the art from the following detailed description and appended claims.

SUMMARY

In accordance with the foregoing, the present invention comprises a method of separating the salt of the desired product from the unreacted salt after Henkel disproportionation in a process for producing aromatic dicarboxylic acids by disproportionation of a salt of an aromatic monocarboxylic acid, which comprises passing both said unreacted salt and said salt of the desired product in an aqueous solution over an adsorbent selected from the group consisting of activated carbons, and thereafter regenerating the carbon bed in place by passing a displacing agent over the carbon bed.

The products to be separated result from a disproportionation or rearrangement type reaction, of the type described in U.S. Pat. Nos. 2,823,231; 3,671,578; and 3,766,258.) In the preferred embodiment, the dipotassium salt of 2,6-NDA, 2,6 K2NDA, is separated from unconverted feed components comprising potassium salts of 1- and 2-naphthoic acid in an aqueous solution of the disproportionation reaction product, by passing said aqueous solution over activated carbon, recovering the K2NDA, displacing the adsorbed potassium naphthoate from the activated carbon with a water soluble displacing agent, and regenerating the activated carbon.

DETAILED DESCRIPTION OF THE INVENTION

A method known in the art for preparing 2,6-NDA, involves a disproportionation or rearrangement reaction. This reaction disproportionates a feed of aromatic monoacid salts and produces a product comprising mainly a single thermodynamically favored disalt product. Potassium is the economically preferred cation for the salts. A catalyst, typically a Group IIB metal salt or oxide, is used at levels of up to 10 weight percent to increase the disproportionation reaction rate. Additional base, typically as alkali carbonate, can be added to the reaction mixture and helps increase yield of the desired product. After the disproportionation reaction, the product is typically dissolved in water. This separates out the aromatic core molecule produced by the disproportionation reaction, the reaction medium, and the catalyst as separate phases with the unconverted feed and the desired reaction product dissolved in the aqueous phase. As mentioned above, the method for purification of 2,6-NDA has typically been crystallization or precipitation with carbon dioxide, however it has been discovered in the present invention that activated carbon is suitable for use in the separation and recycling of unreacted feed components from salts of aromatic dicarboxylic acids after a disproportionation reaction. After separating the reaction medium (naphthalene) and filtering the catalyst (solid zinc oxide), the dissolved salts are ready for treatment with the solid adsorbent.

In the present invention it has been discovered that in a process for producing 2,6-NDA which incorporates a step of disproportionation or rearrangement of potassium naphthoate to produce the dipotassium salt 2,6-K2NDA, activated carbon can be used as an adsorbent to separate unconverted potassium naphthoate from the desired product.

In addition, it has been discovered in the present invention that the activated carbon can be regenerated using a simple cyclic adsorption process with a facile regeneration accomplished by a wide variety of displacing agents. In the art, spent activated carbon is most often discarded or regenerated via a high temperature thermal process. The temperatures required are typically as high as 900° C. and these temperatures would result in the destruction of any organic products adsorbed on the carbon before they could be recycled for conversion into desired products.

Finally, the potassium naphthoate is recovered from the activated carbon beds in a usable form and can be recycled for use in a larger process for making 2,6-NDA.

The results described herein are unexpected because activated carbon is typically used to adsorb trace levels of materials from a solution, not percent level impurities in the presence of about ten times excess of a very similar molecule. It is unexpected for the activated carbon to demonstrate such a strong selectivity difference for two adsorbates that are reasonably similar in molecular weight and structure, such as potassium naphthoate and 2,6-dipotassium naphthalene dicarboxylic acid.

In addition to the alkali metal salt of naphthoic acid, the salts of other aromatic mono- or polycarboxylic acids can be used, however this process is particularly effective for separating unreacted potassium naphthoate from 2,6-dipotassium naphthalene dicarboxylate.

In carrying out the disproportionation of aromatic mono- or dicarboxylic acids it is advantageous to use the alkali metal salts, preferably the potassium salt or the sodium salt is used. The lithium, rubidium and cesium salts can also be used. Cesium is a better cation for the Henkel reaction than potassium, but is very expensive compared to potassium. Potassium works better than sodium and the improved performance supports the price differential between sodium and potassium. Lithium does not work as well as sodium and is extremely toxic. Rubidium is rare in the environment and therefore is very expensive. Also, mixtures of salts of two different metals, such as, sodium and potassium can be used. In the place of the salts, mixtures can also be used which are transformed into the salts upon heating. For example, mixtures of carboxylic acid, anhydrides and alkali metal carbonates can be used. Note however, anhydrides are not likely to run correctly in a Henkel reaction unless the anhydride is mixed with excess alkali and allowed to react to a disalt before heating to Henkel reaction temperatures.

The disproportionation or rearrangement reaction is carried out in an inert, substantially oxygen-free atmosphere in order to prevent decomposition. It is advantageous to perform the rearrangement reaction in an atmosphere of inert gases or vapors such as carbon dioxide, nitrogen, the noble gases, methane, ethane, propane etc., at atmospheric or superatmospheric pressure.

In the preferred embodiment potassium naphthoate is disproportionated in the presence of a thermally stable solvent and a zinc catalyst as described in copending U.S. Ser. No. 60/151,577, incorporated herein by reference in its entirety.

In the integrated process of copending U.S. Ser. No. 60/151,577 the aqueous salt is directed to the disproportionation section in a slurry. Just prior to the disproportionation reactor is a two-stage water removal section. To prepare the feed for the disproportionation reaction, water from the aqueous salt solution of potassium naphthoate is evaporated with hot recycled solvent. The water concentration of the disproportionation feed should be reduced to avoid significant decarboxylation of the disproportionation reaction product. The aqueous potassium naphthoate is contacted with solvent to flash water and is then pumped into the disproportionation reactor as a slurry. Just prior to the reactor, the disproportionation reaction Zn catalyst is added to the slurry. The crude product in the slurry with solvent and catalyst are fed into a furnace for heating in preparation for the disproportionation.

Suitable temperatures for the disproportionation reaction are in the range of from about 340° C. to 500°. Better results are observed where the temperature is from about 400° C. to 480°. The preferred temperature is from about 440° C. to 460° C.

Suitable $CO_2$ pressures for the disproportionation are from about 200 to 10,000 psi. A more preferred range is from about 350 to 1100 psi. To accelerate the reaction and suppress the occurrence of side reactions the reaction temperature is preferably about 450° C. and the pressure is about 850 psi to 950 psi.

The disproportionation reaction produces the salt of the desired 2,6-NDA product, (K2NDA), which can include isomers. The disproportionation reaction can include two, or even three, stages to push conversion. The disproportionation effluent solids (in solvent) consist primarily of 2,6 K2NDA, 2,3 K2NDA (isomer intermediate), unreacted KNA, catalyst, and trace coke.

In copending U.S. Ser. No. 60/151,577 the liquid/solid phase product exits the disproportionation reactor where the pressure is, say about 800 to 1100 psi. The liquid/solid phase product exits the disproportionation reactor and enters a tapered bore where there is a significant pressure drop. The result of the pressure letdown is that the solvent is flashed and the liquid/solid phase becomes gas/solid. Then the gas/solid phase products enter the first of two stripper cyclones where each of the two stripper cyclones is connected to a second stage cyclone. Each second stage cyclone is equipped to return additional separated solids to the stripping cyclone to which it is connected. In these cyclones solids are separated and gases exit and are recycled. This is discussed in further detail in U.S. patent application Ser. No. 60/151,498, filed of even date, and incorporated by reference herein in its entirety.

The separation of the solvent and catalyst can also be carried out using other methods known in the art, as discussed above.

After separating the solvent and filtering the solid catalyst, the crude product is dissolved in water. At this point the dissolved salts are ready for treating with the solid adsorbent in accordance with the present invention which provides a very energy efficient means of recovering the unreacted potassium naphthoate and separating the dipotassium salts.

Adsorbents that function appropriately for use in the present invention are activated carbons. A large number of commercially available activated carbons are suitable, but preferred results were obtained using those described as high purity carbons. High purity carbons have lowered metal impurities contents, typically less than 2 wt % metals.

Activated carbons employed with good results in Examples 1 through 4 were CPG, 12×40 mesh; CAL, 12×40 mesh; F400; and PCB, 12×30, all commercially available from Calgon Carbon Corporation. Activated carbons can be produced by pyrolyzing organic materials such as coal, peat, or coconut shells under high temperatures in a nonoxidizing environment. The raw carbonaceous material can also be mixed with a binding agent to form a granular material. The pyrolized carbonaceous material can then be activated by steaming to create a high capacity, high surface area adsorbent. Raw materials with low metals content are preferred as they produce more pure activated carbons with a final lower metals content although an acid wash step can be used leach some of the residual metals from the as produced activated carbon.

These carbons are typically washed with acid to remove leachable metals, but still contain percentage levels of metal oxides in the amorphous carbon matrix. In the examples herein, these activated carbons were washed prior to use with dilute potassium hydroxide to prevent the precipitation of insoluble acids on the acidic carbon surfaces by neutralization of the acid sites on the surface of the carbon.

In the process of this invention, the product of a rearrangement reaction, containing unreacted potassium naphthoate and 2,6-dipotassium naphthalene dicarboxylic acid is dissolved in water and passed over activated carbon. Generally, the concentration of the dissolved salts in the aqueous phase is as high as possible to improve the throughput of the process. The concentration of dissolved salts may be from about 10 to 50 wt %, but in the examples of this invention the concentration was about 20–30%, preferably about 25 weight percent 2,6-K2NDA and KNA with the KNA being about 10wt % on a 2,6-K2NDA basis.

It is desirable to control the pH of the aqueous solution to prevent precipitation of the insoluble carboxylic acids in the activated carbon bed. The pH of the aqueous solution is typically in the range of 10 to 12, but it can be buffered down to as low as about 8.5, if desired, with, for example, carbon dioxide. Lower pH's risk the precipitation of the corresponding carboxylic acids in the activated carbon bed.

The feed is metered to the adsorption beds at a rate such that the mobile phase can equilibrate with the solid phase. For adsorption on carbon from a liquid phase, this is generally about one to three bed weights of aqueous feed per hour. The rate is governed by mass transfer within the carbon particles and from the aqueous solution to the carbon particles. Smaller activated carbon particles increase both mass transfer rates but also dramatically increase the pressure drop across the bed. At equilibrium, bed life is determined by the capacity of the adsorbent for the unconverted feed and the concentration of the unconverted feed in the aqueous stream. The activated carbons investigated herein typically hold 0.25 to 0.30 lb of 2-KNA per lb of carbon at equilibrium with a feed solution containing approximately 2 wt % 2-KNA.

The temperature and pressure at which the adsorption columns are run are not critical. The temperature can vary over a wide range, such as, for example, 25° C. to 60° C. without observing a difference in the capacity of the carbon. Pressure will be determined by factors such as pressure drop requirements for the adsorption beds or by energy conservation strategies within a process unit.

Adsorption runs in the laboratory have shown that, on a 2,6-K2NDA basis, the product can contain as little as 50 ppm 2-KNA after adsorption which is well within the required specification for monofunctional impurities in the final product. The carbon has an added benefit in that it will, to some extent, remove color bodies from the final product by preferential adsorption.

Another embodiment of the present invention comprises regeneration of the carbon beds in place. This embodiment envisions a series of beds of activated carbon, such that the aqueous solution can be contacted with a first bed until the adsorbent in the bed is expended. Then the bed is taken off-line and the aqueous solution of disproportionation reaction product is fed to another adsorption bed in the adsorption train.

Figure 1:
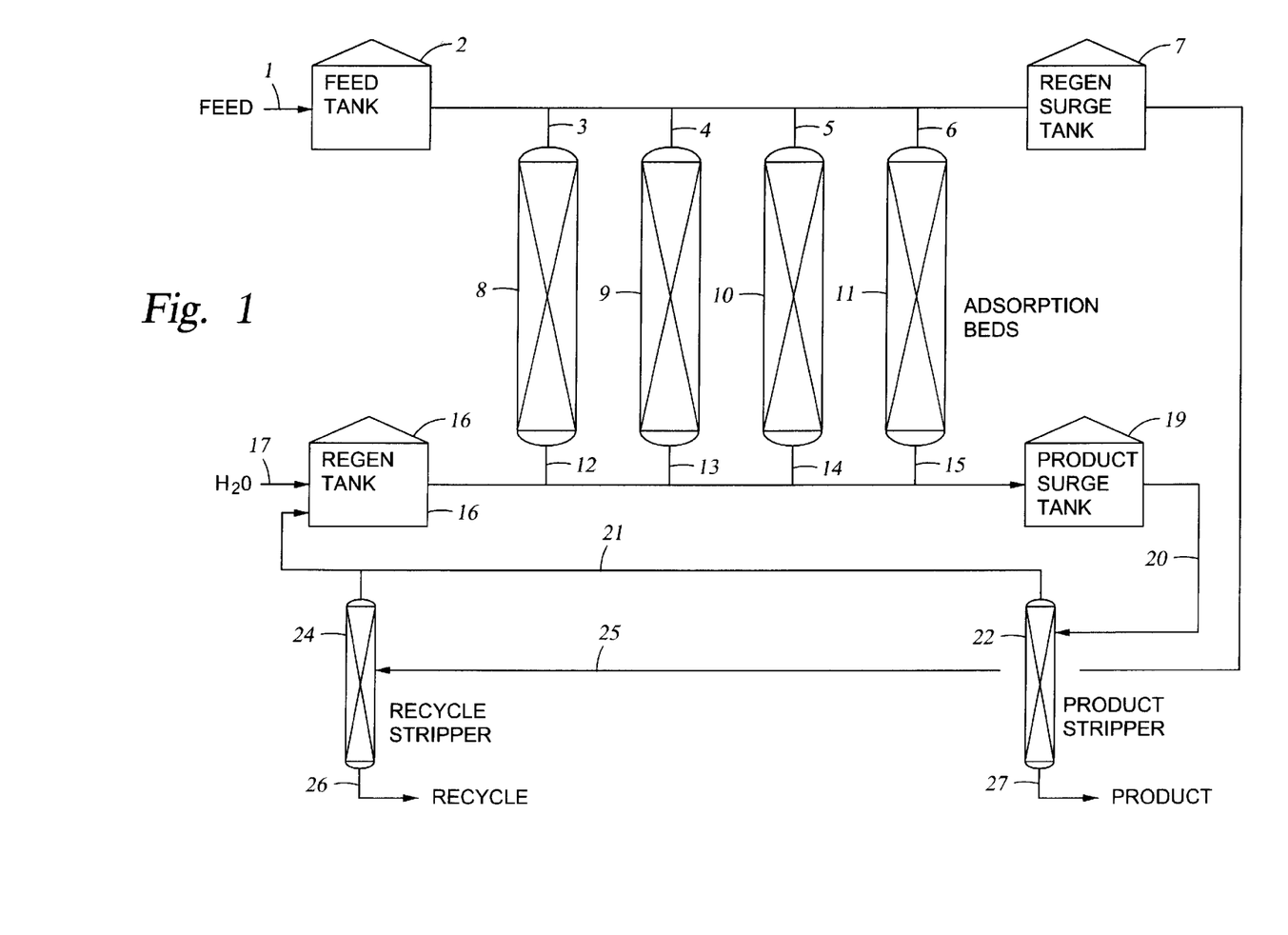
FIG. 1 is a schematic drawing of a potassium naphthoate removal system.

The regeneration of the carbon beds in place is a very attractive feature of this invention. Referring to FIG. 1, it is noted that a number of beds can be operated together in a carousel fashion to achieve pseudo steady state behavior on the product and regeneration streams. When a bed is taken off-line, the spent bed is preferably backwashed first with about 1 bed volume of water to displace any 2,6-K2NDA or other unadsorbed feed material back to the feed tank for the adsorption unit. This step helps to increase the per pass yield of the adsorption section by minimizing the amount of 2,6-K2NDA that is removed from the adsorption bed in the regeneration stream. Additionally, it is also preferred to operate the backwash and regeneration steps in a counter-current fashion to the adsorption step to maximize the efficiency of the adsorption bed.

Regeneration in laboratory column experiments has been performed with a solution of displacing agent in water in countercurrent flow at a rate of 1–3 bed weights per hour. The displacing agent is an organic molecule that has a reasonable affinity for adsorption on activated carbon and is capable of displacing the weakly bound potassium naphthoate from the carbon.

The displacing agent can suitably be selected from water soluble alcohols, esters or acids having one to four carbon atoms. Examples include, but are not limited to, methanol, acetone, isopropyl alcohol, tetrahydrofuran, and ethyl acetate. P-xylene works well as a displacing agent, but is not water soluble. While many organics can displace the KNA's from the activated carbon, a significant amount of water is required to solubilize the desorbed KNA's. A mass balance on the effluent of the adsorption and desorption experiments indicates that this achieves essentially complete regeneration of the bed.

Good results were achieved regenerating the activated carbon beds using tetrahydrofuran. Using 20% tetrahydrofuran in water in the regeneration stream, a bed of adsorbent can be regenerated with about 15 bed weights of regenerant solution. The tetrahydrofuran can be easily removed from the aqueous solution of the desorbed potassium naphthoate by steam stripping and can be recycled for desorption. After the regeneration step is complete, it is likely that a second backwash step of about 1 bed weight of water should be performed. After regeneration, the activated carbon can be reused to treat more disproportionation reaction product.

A drawing of a process incorporating the adsorption methods of this invention is shown in FIG. 1. An aqueous solution of KNA and K2NDA 1 from which solvent and catalyst has been removed enters the feed tank 2. Optionally, the feed to tank 2 can be pH adjusted by the addition of acid of base to the solution to maintain the tank contents in a desired pH region. The aqueous solution then enters through line 3 to the first of a series, 8, of adsorption beds, 8–11. The K2NDA exits through lines 12–15 and enters a product surge tank, 19. The product is then directed through line 20 to a product stripper 22, where the regeneration solvent is removed in an overhead stream 21 and the K2NDA product exits as a bottoms product free, or substantially free, of regeneration solvent at 27. The number of four beds is just used for illustration; the invention contemplates more or less. The adsorption beds are manifolded with valves in such a way that feed can be put into any one of the beds and product from that bed can be fed to any other bed in the train. Furthermore, the manifolding allows for the isolation of a bed during the regeneration phase. The piping manifold is designed so as to minimize dead volume and retained deadlegs which can substantially reduce the efficiency of the adsorption beds. When the activated carbon in the first adsorption bed 8 is depleted, feed coming in is then directed through line 4 into bed 9; then through line 5 to bed 10, and line 6 to bed 11, etc. Another aspect of the invention is that the adsorption beds are regenerated in place. Water is added as needed by 17 to makeup tetrahydrofuran in the regeneration tank 16 and directed countercurrently through line 12 into bed 8 after it has been taken off line and the displacing agent exits 3 with KNA and is directed to the regeneration surge tank 7. The solution of displacing agent and KNA is then directed from 7 to the recycle stripper, 24 where the KNA solution is stripped with steam or other inert gas (nitrogen, methane, etc.) and can be recycled in an integrated NDA process via 26, and the displacing agent is returned to the regeneration tank via 21. The water containing overheaded regeneration solvent is directed to tank 16 for reuse in the separation process.

The following examples will serve to illustrate specific embodiments of the invention disclosed herein. These examples are intended only as a means of illustration and should not be construed as limiting the scope of the invention in any way. Those skilled in the art will recognize many variations which may be made without departing from the spirit of the disclosed invention.

EXAMPLES

A number of laboratory scale experiments were performed in both batch contacting mode to screen adsorbents and in a flow column mode to investigate the behavior of the adsorbent/solution system. Using the batch data adsorbents can be quickly screened. Data are also useful to generate adsorption isotherms which can be used to at least qualitatively predict system behavior in an adsorption column.

Examples 1–12

Figure 2:
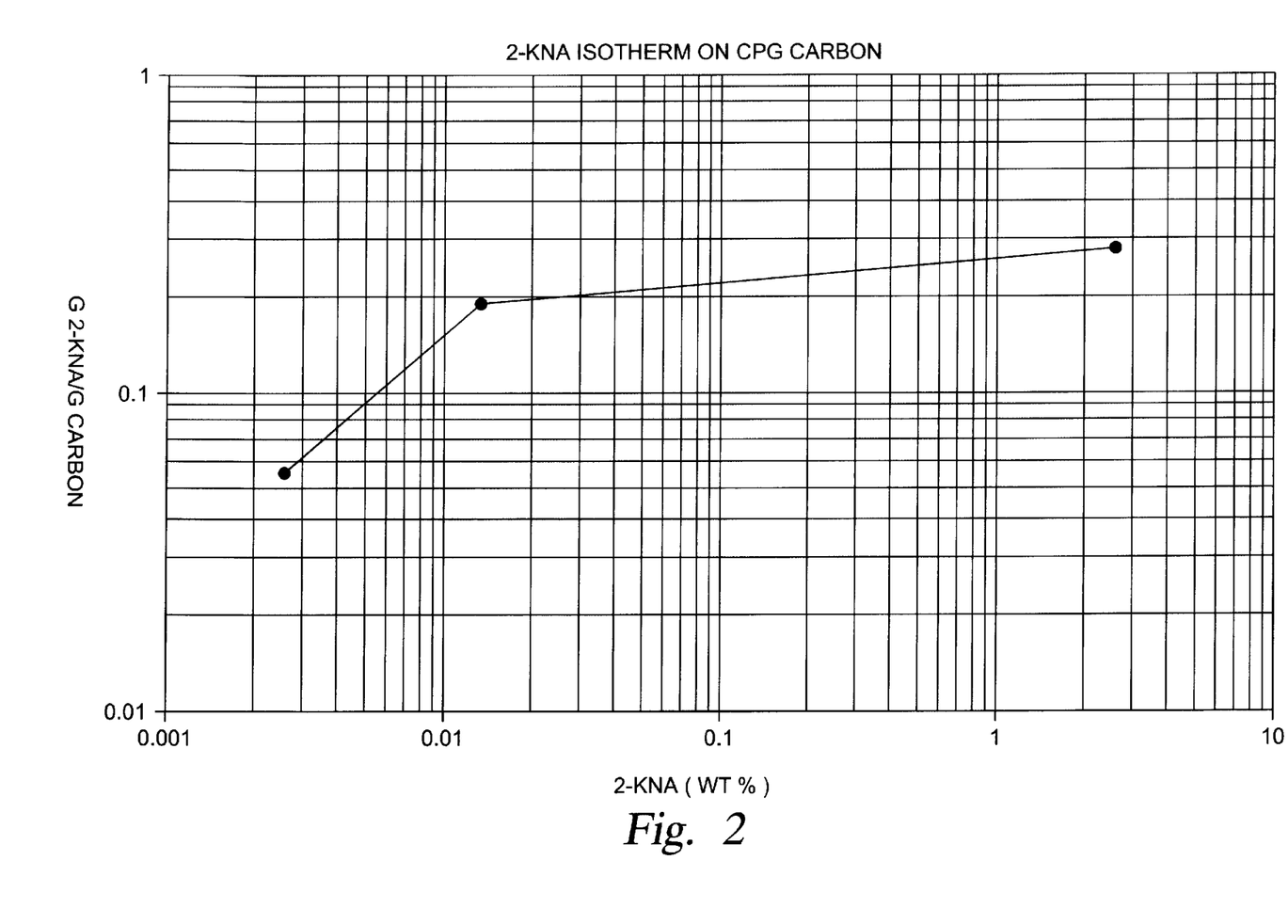
FIG. 2 shows as a graph the considerable affinity that CPG activated carbon has for 2-potassium naphthoate.

Batch screening experiments were performed by stirring solutions of 2-KNA or 2,6-K2NDA or combinations of solutes both in glass vials with an adsorbent sample overnight at 25° C. in a phase ratio of 10 to 1. Typically, the impurities (1-KNA, 2-KNA, or 2,3-K2NDA) were charged at 2% in the aqueous solutions while 2,6-K2NDA was charged at 15–20% to determine the selectivity of the adsorbents for the impurities species in the presence of large amounts of 2,6-K2NDA. Before testing, the adsorbents were prepared by washing with deionized water and oven drying to get an accurate weight on the adsorbent phase. These batch screening experiments show that the activated carbons possess the best adsorption capacity. An adsorption isotherm for the adsorption of 2-KNA on CPG carbon is presented in FIG. 2 and demonstrates graphically the considerable affinity that CPG carbon has for 2-KNA. The polymeric adsorbent resins have some capacity for 2-KNA, but it is not as good as the activated carbons. The zeolitic adsorbents possessed poor capacity for 2-KNA and are expected to perform poorly. Furthermore, the zeolites are somewhat unstable in basic solutions as they tend to slowly dissolve.

A large number of activated carbons are commercially available, but the focus was on "high purity" carbons to minimize metals contamination of the adsorption product. These carbons are typically washed with acid to remove leachable metals, but still contain percent levels of metal oxides in the amorphous carbon matrix. To prevent the precipitation of the insoluble acids on the carbons by neutralization with acid sites on the surface of the carbon, a procedure was employed wherein the carbons were first washed with dilute potassium hydroxide. The caustic wash can be carried out in batch or continuous mode and involves letting the activated carbon sit in the presence of a dilute potassium hydroxide solution before rinsing with deionized water to remove entrained potassium hydroxide.

Figure 3:
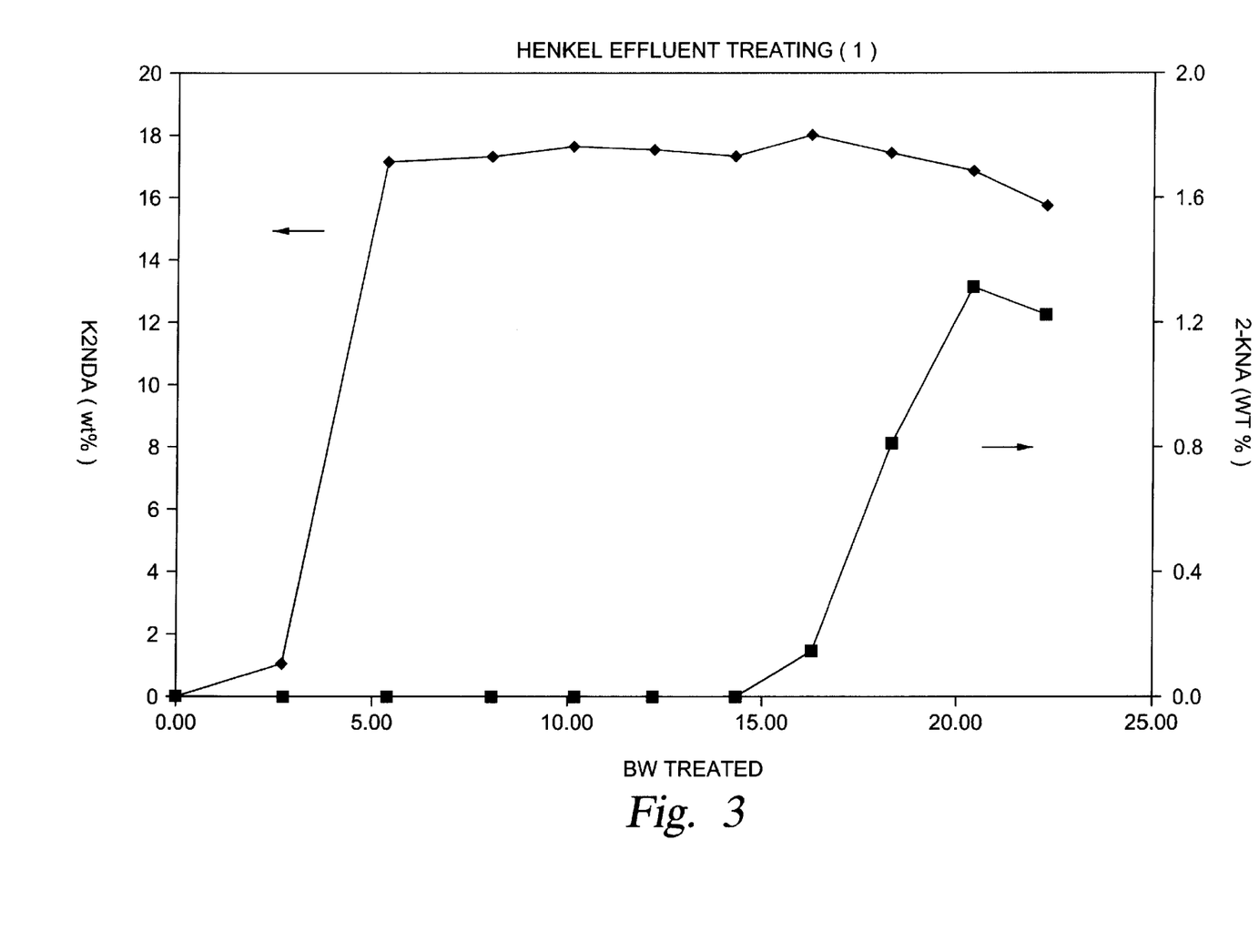
FIG. 3 shows as a graph the amount of adsorption of 2-potassium naphthoate from a simulated disproportionation reactor on one cycle of CPG carbon.
Figure 4:
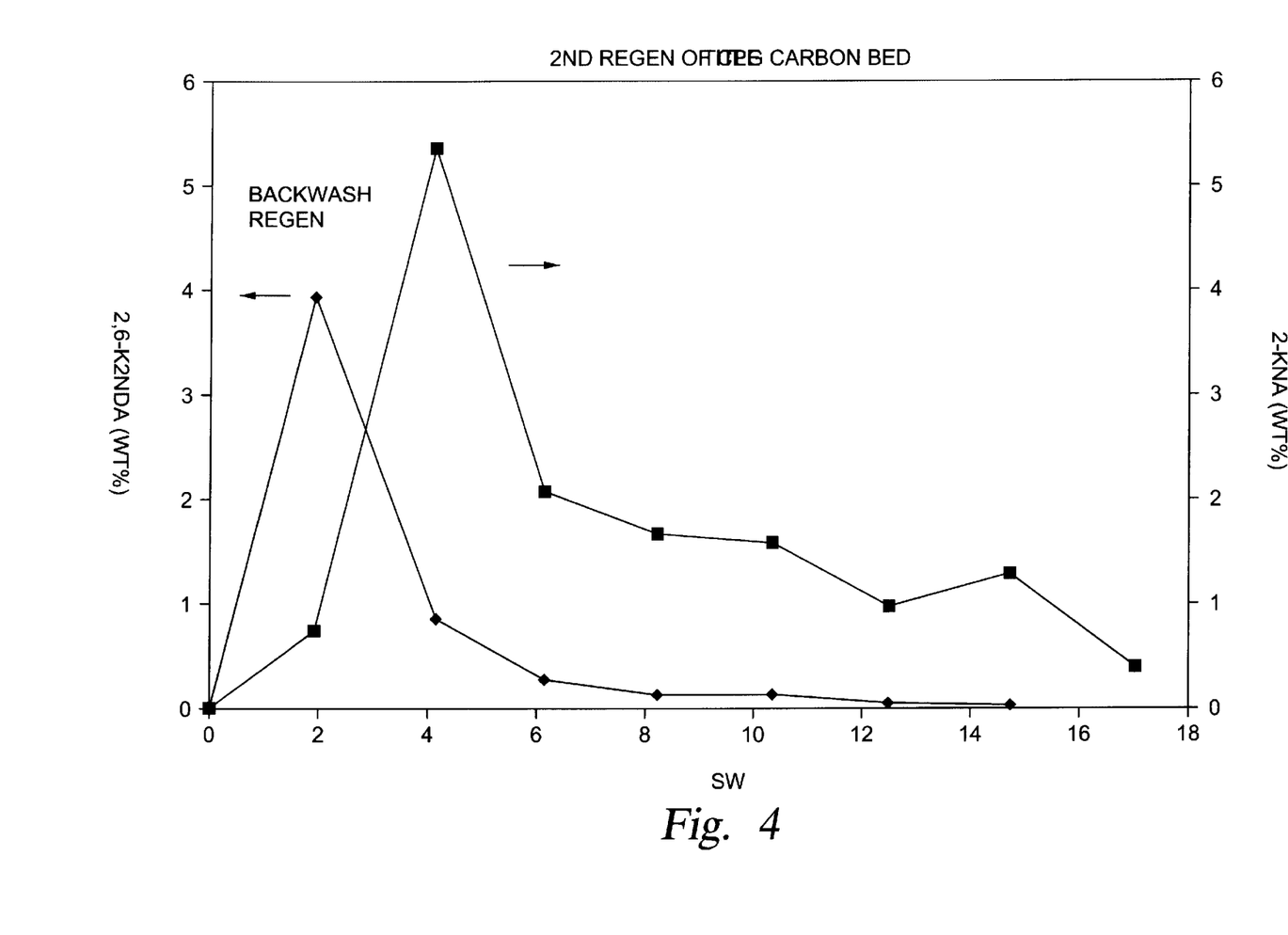
FIG. 4 shows as a graph the regeneration of CPG carbon with 20% tetrahydrofuran solution in water.

The flow adsorption experiments consisted of passing an aqueous solution of 2-KNA and 2,6-K2NDA through a ⅝ inch diameter glass jacketed column containing activated carbon. The bed temperature was maintained at 40° C. by circulating warm ethylene glycol through the column jacket. The feed solution was pumped through the column at weight hourly space velocities (WHSV's) of 1–4. After charging a dried and weighed activated carbon sample to the column, the bed was degassed by flooding the bed under vacuum to removed trapped air. During operation, the effluent was routinely sampled to determine the levels of impurities in the effluent via ion chromatography. After the treating operation had the bed was loaded with monofunctional impurities, the regeneration step was tested by feeding a 20% tetrahydrofuran in water solution. Regeneration was performed counter current to the adsorption operation. FIGS. 3 and 4 show the concentrations of 2,6-K2NDA and 2-KNA in the outlet of the column under adsorption and regeneration conditions, respectively. Ion chromatography of effluent samples determined that 2-KNA levels were as low as 50 ppm (on K2NDA) in the adsorption effluent. By operating the bed in a counter current mode, both good recovery and purity are obtained in the adsorption process.

Table 1 gives a list of the adsorbents tested in the laboratory and the adsorbates tested with those adsorbents. Although both 1- and 2-KNA are expected to be in the disproportionation reactor effluent when mixed methylnaphthalenes are used as naphthoic acid precursor, 2-KNA was primarily used in the examples for consistency in analyzing the results.

TABLE 1

| | Adsorbent | 1-KNA | 2-KNA | 2,6-K2NDA | 2,3-K2NDA |
|---|---|---|---|---|---|
| Example 1 | Calgon CPG, 12 × 40 mesh | X | X | X | X |
| Example 2 | Calgon CAL, 12 × 40 | | X | X | |
| Example 3 | Calgon F400 | | X | X | |
| Example 4 | Calgon PCB, 12 × 30 | | X | X | |
| Example 5 | Rohm and Haas XAD-2 | | X | X | |
| Example 6 | Rohm and Haas XAD-4 | X | X | X | |
| Example 7 | Rohm and Haas XAD-7 | | X | X | |
| Example 8 | Davisil 646 silica, 35 × 60 | | X | | X |
| Example 9 | Alcoa F1 alumina, 14 × 28 | | X | | X |
| Example 10 | Linde Zeolite X, 1/16" extrudate | | X | X | X |
| Example 11 | Zeolyst Zeolite Y, powder | | X | X | X |
| Example 12 | HZSM-5, 1/16" extrudate | | X | | X |

Examples 13–19

In Examples 13 through 19 different displacing agents were tested. In these examples, a 5% solution of 2-KNA dissolved in water was contacted with a CPG carbon in a 10:1 ratio. The two phases were contacted overnight. After the equilibration period, 20% by weight of the displacing agent was added to the solution and stirred for 4 hours. A sample was then taken to determine which of the displacing agents was the most efficient. The results are recorded in Table 2.

TABLE 2

| | Displacing Agent | Wt % 2-KNA |
|---|---|---|
| Example 13 | P-xylene | 4.57 |
| Example 14 | Methanol | 2.70 |
| Example 15 | Acetone | 3.38 |
| Example 16 | Isopropyl Alcohol | 3.42 |
| Example 17 | Tetrahydrofuran | 3.96 |
| Example 18 | Ethylacetate | 3.48 |
| Example 19 | Blank Control | 2.52 |

As can be seen from the data in Table 2, p-xylene was the strongest displacing agent, but it is not water soluble. It is assumed that for reliable operation in an adsorption column that a single phase would be required. Of the water soluble organics, tetrahydrofuran was the most efficient at displacing 2-KNA from the activated carbon. As a cyclic ether, tetrahydrofuran also has the advantage that it is reasonably stable against hydrolysis or esterification.

Example 20

Figure 5:
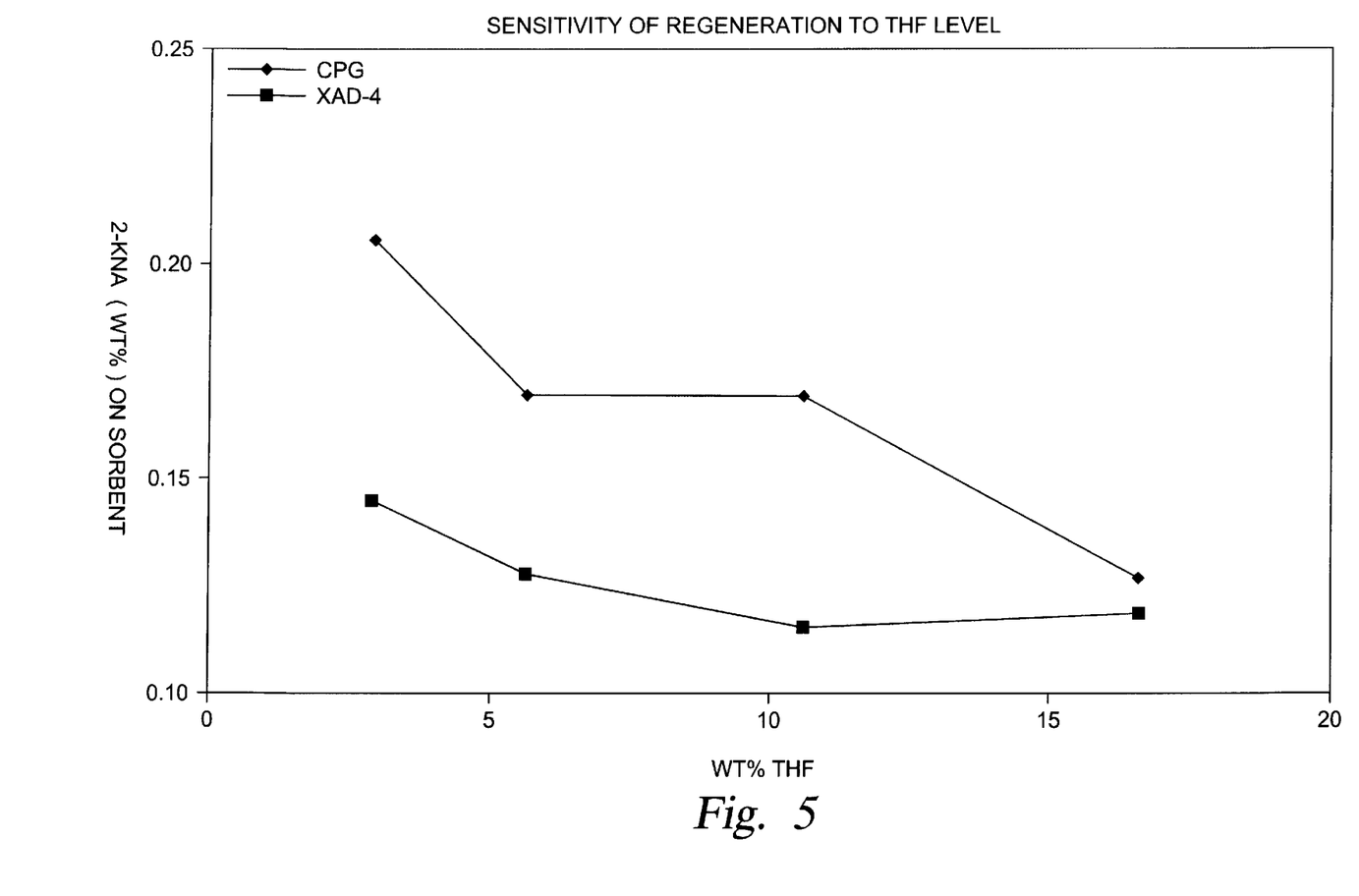
FIG. 5 shows as a graph the sensitivity of the regeneration process to the concentration of tetrahydrofuran.

In this example, an activated carbon and adsorbent resin, Rohm and Haas XAD-4, were equilibrated with 2-KNA solutions. Then varying levels of tetrahydrofuran were added to the supernatant solution to displace the 2-KNA from the adsorbent. The results are shown in the graph in FIG. 5. The graph in FIG. 5 shows that reasonably high levels of displacing agent are required to remove 2-KNA from the solid adsorbents. Even at levels of tetrahydrofuran approaching 20 wt %, the carbon still contains as much as 10 wt % 2-KNA. This demonstrates that the 2-KNA is more strongly sorbed and that the displacing agent works largely by mass action.

I claim:

1. In a process for producing aromatic dicarboxylic acids which incorporates disproportionation of a salt of an aromatic carboxylic acid to produce unreacted salt of an aromatic carboxylic acid and the salt of the desired aromatic dicarboxylic acid, a method for separating the salt of the desired product from the unreacted salt which comprises passing both said unreacted salt and said salt of the desired product in an aqueous solution over a bed of adsorbent comprising activated carbon.

2. The process of claim 1 wherein the unreacted salt is potassium naphthoate, and the salt of the desired product is the dipotassium salt of naphthalene dicarboxylic acid 2,6-K2NDA.

3. The process of claim 1 wherein the aqueous solution of unreacted potassium naphthoate and dipotassium salt of 2,6-naphthalene dicarboxylic acid contains about 1–50% of the combined salts in water.

4. The process of claim 3 wherein the aqueous solution contains about 10–40% combined salts in water.

5. The process of claim 4 wherein the aqueous solution contains about 20–30% combined salts in water.

6. The process of claim 1 wherein said adsorbent is activated carbon.

7. The process of claim 6 wherein said activated carbon adsorbent further comprises a high purity carbon that has been washed to remove leachable metals.

8. The process of claim 7 wherein said high purity activated carbon is washed with an aqueous potassium hydroxide solution before first use.

9. The process of claim 1 wherein said adsorbent bed further comprises multiple adsorbent beds in a series.

10. The process of claim 9 wherein said aqueous solution is treated over an adsorbent bed until said bed is expended and then said aqueous solution is directed to the next adsorbent bed in the series.

11. The process of claim 10 which further comprises regenerating the expended bed by countercurrently backwashing the bed with water and then countercurrently passing displacing agent over the bed.

12. The process of claim 11 wherein the bed is countercurrently backwashed with about 1–3 bed volumes of water.

13. The process of claim 11 further comprising passing said displacing agent countercurrently over the bed at a rate of about 0.1–10 bed weights per hour.

14. The process of claim 11 wherein said displacing agent selected from the group consisting of at least partially water soluble alcohols, ethers or esters characterized by having from one to six carbons.

15. The process of claim 14 wherein the water soluble displacing agent is selected from the group consisting of methanol, acetone, isopropyl alcohol, ethyl acetate, and tetrahydrofuran.

16. The process of claim 15 wherein the water soluble displacing agent is tetrahydrofuran.

17. The process of claim 11 wherein said displacing agent is in a solution of water in an amount of 5–80%.

18. The process of claim 17 wherein said displacing agent is in a solution of water in an amount of 15–50%.

19. The process of claim 18 wherein said displacing agent is in a solution of water in an amount of about 20% or the solubility limit of the solvent in the aqueous solution, whichever is higher.

20. In a process for producing 2,6-naphthalene dicarboxylic acid by disproportionation of potassium naphthoate to produce the dipotassium salt of 2,6-naphthalene dicarboxylic acid and unreacted 1- and 2-potassium napthoate, a method for separating said potassium naphthoate from the dipotassium salt of napthalene dicarboxylic acid which comprises:

passing both said potassium naphthoate and said dipotassium salt in an aqueous solution over the first of a series of two to six beds containing adsorbent comprising activated carbon until said activated carbon is expended;

directing said aqueous solution to the second bed, or subsequent bed in the series, of activated carbon; backwashing the expended bed with water; and regenerating the expended bed by countercurrently passing a saturated solution of tetrahydrofuran in water over the expended bed.

* * * * *